United States Patent [19]

Coelho et al.

[11] Patent Number: 5,243,833
[45] Date of Patent: Sep. 14, 1993

[54] DEVICE FOR THAWING FROZEN TRANSFUSION MATERIAL AND METHOD THEREFORE

[75] Inventors: Philip H. Coelho; Terry Wolf, both of Rancho Cordova, Calif.

[73] Assignee: Instacool Inc. of North America, Rancho Cordova, Calif.

[21] Appl. No.: 789,696

[22] Filed: Nov. 8, 1991

[51] Int. Cl.$^5$ .............................. F25D 17/02
[52] U.S. Cl. ...................... 62/376; 62/438; 604/903; 604/409; 165/80.5; 165/104.28; 392/470
[58] Field of Search ............. 62/373, 376, 435, 438, 62/64; 604/903, 403, 409; 165/80.5, 84, 104.31, 104.28; 392/470

[56] References Cited

U.S. PATENT DOCUMENTS

| 2,845,929 | 8/1958 | Strumia | 604/903 |
| 3,586,097 | 6/1971 | Bender et al. | 165/65 |
| 4,563,883 | 1/1986 | Sitte | 62/64 |
| 4,707,587 | 11/1987 | Greenblatt | 219/299 |
| 4,715,195 | 12/1987 | Kucza | 62/376 |

FOREIGN PATENT DOCUMENTS

| 137147 | 10/1979 | Japan . | |
| 180754 | 8/1987 | Japan . | |
| 9117641 | 11/1991 | PCT Int'l Appl. | 392/470 |
| 2014583 | 8/1979 | United Kingdom . | |

OTHER PUBLICATIONS

Lifesource Advanced Blood Bank Systems, 1990 Flash System and Related Products Catalog.

Primary Examiner—Albert J. Makay
Assistant Examiner—William C. Doerrler
Attorney, Agent, or Firm—Bernhard Kreten

[57] ABSTRACT

A method and device for thawing pouches of frozen transfusion material including a membrane which provides a barrier within an interior of the device with the membrane receiving the pouches of frozen material therewithin. The interior of the device includes a sump having thawing fluid stored therein and maintained at a constant target temperature which is to be achieved by the frozen transfusion material to be thawed. The pouch of material to be thawed, after placement within the membrane, is exposed (through the membrane) to hydrostatic forces associated with the fluid in the sump collapsing the membrane on the pouch while pulsating jets impinge indirectly upon the pouch through the membrane. In this way, as the contents within the pouch thaw, circulation of the fluid within the pouch occurs for more rapid realization of the target temperature for the fluid within the pouch.

19 Claims, 6 Drawing Sheets

DEVICE FOR THAWING FROZEN TRANSFUSION MATERIAL AND METHOD THEREFORE

FIELD OF THE INVENTION

This invention relates generally to instrumentalities which facilitate the thawing of transfusionable materials such as blood, platelets or plasma or other human tissues or pharmaceutical products such as antibiotics from a frozen to a liquid state to allow their transfusion a short time thereafter.

BACKGROUND OF THE INVENTION

Thermolabile products such as blood, platelets, tissue or plasma define a resource which must be husbanded very carefully especially in an era where the demand for blood increases as the population grows but the source of blood becomes more suspect with the continuing discovery of increasingly prevalent blood-transferable diseases.

Other thermolabile pharmaceutical products like antibiotics are also a valuable resource which must be carefully guided through all temperature ranges so that the rated potency is maintained.

For instance, a typical operatory scenario involves some forecasting on the volume of blood to be required during a surgical procedure, but there is a tendency to be conservative in the estimation of total units of blood or plasma required due to the above-noted market pressures. This sometimes leads to shortages during an operation. Moreover, events may transpire during the course of surgery which dictate an immediate need for additional blood supplies which either can not be contemplated at the initiation of the surgery or, for example, occur as the result of emergency procedures.

Heretofore, pouches within which frozen blood or plasma has been stored are placed within a pan having warm water. The pan is supported on an instrumentality which allows the pan to rock back and forth to aid in the circulation of the water over the pouch to increase the rate at which thawing occurs. At a later stage in the thawing process, personnel will manually knead the pouch to accelerate the thawing process.

Several difficulties attend the current state of the art technique. For one thing, some pouches, especially during the freezing process may be cracked so that upon thawing, the tray, water and attendant who kneads the pouch may become contaminated with the blood should the pouch break. The corollary to such a fracture is that the entire area exposed to the blood has now been contaminated. The cleanup process may conflict with the exigencies of the surgical necessity, providing a risk which is needless when one embraces the technology of the instant invention.

A further inefficiency associated with the known prior art involves the actual heat transfer mechanism itself. When contrasted with the instant invention, the process is relatively slow and does not provide the controlled environment that attends the instant invention for optimal regulation of the thawing process especially as it changes phase from solid to liquid and involves minimizing hot spots. It must be borne in mind that these transfusable fluids are thermolabile and therefore deteriorate rapidly in the presence of unwanted temperature profiles. Thus, the water placed in the tray may induce deleterious localized heating of the fluid thereby lowering the quality of the blood, platelets, plasma etc. which is ultimately utilized.

A further difficulty that the instant invention solves is that the time-frame during which the surgeon must decide on the need for potential transfusable fluid will have changed when utilizing the instant invention. Stated alternatively, the instant invention thaws the blood or plasma in a shorter amount of time.

The following patents reflect the state of the art of which applicant is aware insofar as these patents appear germane to the patent process. However, it is respectfully stipulated that none of these patents teach singly nor render obvious when considered in any conceivable combination the nexus of the instant invention as set forth hereinafter.

| INVENTOR | PATENT NO. | ISSUE DATE |
|---|---|---|
| Burke | 1,939,334 | December 12, 1933 |
| Kesslinger | 2,034,472 | March 17, 1936 |
| Zarotschenzeff | 2,254,406 | September 2, 1941 |
| Vore | 2,274,284 | February 24, 1942 |
| Stebbins | 2,286,514 | June 16, 1942 |
| Kleist | 2,455,867 | December 7, 1948 |
| Morrison | 2,618,939 | November 25, 1952 |
| Clarke | 2,914,445 | November 24, 1959 |
| Staebler | 2,964,920 | December 20, 1960 |
| Mills | 3,027,734 | April 3, 1962 |
| Morrison | 3,090,134 | May 21, 1963 |
| Morrison | 3,096,627 | July 9, 1963 |
| Rother | 3,263,441 | August 2, 1966 |
| Bagge-Lund | 3,300,994 | January 31, 1967 |
| Pauliukonis | 3,320,757 | May 23, 1967 |
| Eilenberg, et al. | 3,394,469 | July 30, 1968 |
| Thompson | 3,440,831 | April 29, 1969 |
| Lahr, et al. | 3,485,245 | December 23, 1969 |
| Harza | 3,514,969 | June 2, 1970 |
| Anderson | 3,518,033 | June 30, 1970 |
| Ross | 3,545,671 | December 8, 1970 |
| Ersek | 3,612,059 | October 12, 1971 |
| Schwartz | 3,753,357 | August 21, 1973 |
| Dastur | 3,758,257 | September 11, 1973 |
| Howard | 3,774,524 | November 27, 1973 |
| Baker | 3,791,162 | February 12, 1974 |
| Bierley, et al. | 3,844,133 | October 29, 1974 |
| Faust, et al. | 3,875,754 | April 8, 1975 |
| Faust | 3,898,023 | August 5, 1975 |
| Turner | 3,911,918 | October 14, 1975 |
| Anderson, et al. | 3,920,625 | November 18, 1975 |
| Faust, et al. | 3,952,536 | April 27, 1976 |
| Turner | 3,911,918 | October 14, 1975 |
| Anderson, et al. | 3,920,625 | November 18, 1975 |
| Faust, et al. | 3,952,536 | April 27, 1976 |
| Samson, Jr., et al. | 3,954,414 | May 4, 1976 |
| Garber, et al. | 4,025,618 | May 24, 1977 |
| Leonard, et al. | 4,026,669 | May 31, 1977 |
| Harza | 4,044,569 | August 30, 1977 |
| Faust, et al. | 4,090,374 | May 23, 1978 |
| Naftulin | 4,129,131 | December 12, 1978 |
| Seufert | 4,141,887 | February 27, 1979 |
| Hjertstrand, et al. | 4,145,895 | March 27, 1979 |
| Granzow, Jr., et al. | 4,167,663 | September 11, 1979 |
| Shanbrom | 4,188,318 | February 12, 1980 |
| Faust, et al. | 4,194,369 | March 25, 1980 |
| Pert, et al. | 4,251,995 | February 24, 1981 |
| Seufert | 4,278,592 | July 14, 1981 |
| Le Boeuf | 4,309,592 | January 5, 1982 |
| Sheehan, et al. | 4,322,954 | April 6, 1982 |
| Campbell | 4,343,158 | August 10, 1982 |
| Mather, III, et al. | 4,424,190 | January 3, 1984 |
| Morris | 4,470,264 | September 11, 1984 |
| Toledo-Pereyra | 4,502,295 | March 5, 1985 |
| Douglas-Hamilton | 4,530,816 | July 23, 1985 |
| Shah, et al. | 4,532,414 | July 30, 1985 |
| Hashimoto, et al. | 4,534,183 | August 13, 1985 |
| Kanto, et al. | 4,555,914 | December 3, 1985 |
| Sasaki | 4,583,375 | April 22, 1986 |
| Rose, et al. | 4,627,879 | December 9, 1986 |
| Bilstad, et al. | 4,630,448 | December 23, 1986 |
| Sitte | 4,637,226 | January 20, 1987 |

-continued

| INVENTOR | PATENT NO. | ISSUE DATE |
| --- | --- | --- |
| Foster | 4,638,048 | January 20, 1987 |
| Nagoshi | 4,654,217 | March 31, 1987 |
| Nagoshi | 4,657,768 | April 14, 1987 |
| Sakai | 4,689,963 | September 1, 1987 |
| Polaschegg | 4,713,171 | December 15, 1987 |
| Ammerman | 4,723,974 | February 9, 1988 |
| Coelho, et al. | 4,730,460 | March 15, 1988 |
| Hashimoto | 4,760,712 | August 2, 1988 |
| Auerbach | 4,801,777 | January 31, 1989 |
| Coelho, et al. | 4,803,842 | February 14, 1989 |
| Wilson | 4,808,159 | February 28, 1989 |
| Liberman | 4,840,034 | June 20, 1989 |
| Liberman | 4,840,035 | June 20, 1989 |
| Nicholas Marchiani Chatelain, et al. | 4,874,033 | October 17, 1989 |
| Stanojevic | 4,906,913 | March 6, 1990 |
| Van Iperen, et al. | 4,923,077 | May 8, 1990 |
| Howard | 4,928,492 | May 29, 1990 |
| White | 4,934,336 | June 19, 1990 |
| Chao | 4,949,555 | August 21, 1990 |
| Gilbert | 4,951,482 | August 28, 1990 |
| Guilhem, et al. | 4,958,506 | September 25, 1990 |
| Nose', et al. | 4,966,709 | October 30, 1990 |
| Richard | 5,029,447 | July 9, 1991 |
| Kanao | JP54-137,147 | October 24, 1979 |

Alan R. Fisher; "The Flexible Froster"; *National Frosted Foods*, INc.; 1939

E. L. Hulland, Swift and Company; "Immersion Freezing of Poultry"; *Refrigeration and Meat Packing Conference*; 1957.

B. C. McKenna, City Products Company; "Economics of coils vs fan or blower units in combination freeze and hold freezers"; *Refrigeration and Meat Packing Conference*; 1957.

J. Clin Pathol; "Studies on the procurement of blood coagulation factor VIII: effects of plasma freezing rate and storage conditions on cryoprecipitate quality"; Edinburgh and South-East Scotland Blood Transfusion Service, Royal Infirmary, Edinburgh; 1985.

NABI, The Quality Source Brochure; Cyto-Therm III; distributed by National Hospital Specialties

SUMMARY OF THE INVENTION

The instant invention is distinguished over the known prior art in a multiplicity of ways. In its elemental form, a reservoir is provided which receives thawing fluid therewithin which is isolated from the transfusing material such as blood or plasma not only by the pouch within which the blood or plasma resides, but also by a membrane which is interposed between the blood pouch and which depends into the reservoir. Thus, should the pouch have a hairline fracture, upon thawing the blood, and if the blood contaminates areas outside the pouch, the contamination will be localized to the interior of the membrane which is configured for expeditious dislodgement from its situ overlying and depending within the reservoir. Replacement with a fresh membrane free from contamination is a minor procedure. Thus, one attribute of the invention is the means by which it takes into account the likelihood of a pouch having a fracture.

The reservoir includes means for storing a thawing fluid and maintaining that fluid at an ideal temperature, typically greater than 2° C., and often as high as 37° C. which is the temperature recommended by the American Association of Blood Banks. Upon deployment of the pouch of transfusing material within the membrane, the membrane depends within the reservoir and the thawing fluid is directed at the membrane in two distinct manners. A first manner involves raising the liquid level of the fluid up around the membrane and the transfusing material within the pouch so that hydrostatic pressure exists on the membrane causing it to collapse so that it conforms to the exterior contour of the pouch. The absence of an air gap between the membrane and the pouch assures that the thermal profile in heat exchange is optimal. A second manner in which the thawing fluid thermally contacts the pouch takes the form of a pulsation in which exterior surfaces of the membrane pocket receive thawing fluid from a nozzle such that the thawing fluid impinges on the membrane pocket and defines a component in which kinetic energy is dissipated by the contact directly against the membrane and indirectly against the pouch, adding further heat transfer from the deceleration of the thawing fluid.

An ancillary benefit attends this pulsation. As the blood, tissue, platelet or plasma or pharmacological product within the pouch starts to thaw, the pulsation defines an area of accelerated thawing which preferably is located at the geometrical center of the pouch on a major side surface of the pouch i.e. away from side edges. Ultimately, the center of the thermolabile, transfusible fluid within the pouch will have been thawed prior to the outer periphery especially because there has been pulsing on two major faces of the pouch. In a preferred form of the invention, two such nozzles are provided one on each side of the pouch and are synchronized to contact the pouch simultaneously, so that equal and opposite forces are experienced on both sides of the pouch, providing forced circulation of the transfusible material as it thaws. This synchronous pulsing also keeps the pouch stable and free from oscillation.

Another benefit of the forced circulation of the thawing fluid within the pouch is that it occurs in a substantially toroidal manner so that there is internal circulation which is simulative of the kneading that heretofore had been practiced by an attendant. By attacking the geometrical center of the bag through the pulsing liquid, the thawing process will have been accelerated.

Other types of kneading could occur by either different orientation of nozzles in their contacting relationship with the pouch or by other means by which the pouch is manipulated. For example, variously shaped platens can move in jaw-like concert to intermittently squeeze the bag. Other forms of vibratory excitation could also provide the similar benefit.

As the result of the above-described structure and methodology, transfusable fluids such as blood, platelets, tissue or plasma or pharmaceutical products such as antibiotics will be delivered ready for transfusion at the optimal temperature in minimal time and thoroughly mixed. Typically less than 15 minutes is required for 250 ml. of plasma to be raised from a frozen state to a temperature of 37° C.

OBJECTS OF THE INVENTION

Accordingly, it is a primary object of the present invention to provide a novel and useful device and method for rapidly thawing frozen transfusion material such as blood, platelets, tissue or plasma or pharmaceutical product or any thermolabile product or transfusible fluid to a liquid state for immediate use, such as in an operation.

A further object of the present invention is to provide a device as characterized above which minimizes the likelihood of contamination should a frozen pouch have a fracture therewithin which would be discernible upon thawing of the frozen pouch. In the event that such a fracture occurs, a primary object of the present invention is to re-initialize the thawing apparatus expeditiously with minimal downtime caused by the contamination.

A further object of the present invention is to provide a device as characterized above which precludes the unwanted existence of hot spots which may degrade the thermolabile product when thawing.

A further object of the present invention is to provide a device as characterized above which benefits from a pulsation coacting against the frozen pouch to provide improved circulation of the thermolabile fluid contained within the pouch thereby accelerating the thawing process.

A further object of the present invention is to provide a device as characterized above which does not require the attention of personnel and therefore allows the thawing process to be performed unattended.

A further object of the present invention is to provide a device as characterized above which is automated and regulated such that the thawing process, while unattended provides uniform results.

A further object of the present invention is to provide a device as characterized above which lends itself to mass production techniques, is safe and easy to use, and is extremely durable in construction.

A further object of the present invention is to provide a device as characterized above which substantially shortens the amount of time required for thawing frozen thermolabile fluids contained in pouches especially in emergency situations or involving the requirement of blood for lifesaving situations.

Viewed from one vantage point, it is an object of the present invention to provide a device for transferring heat with respect to a thermolabile product which is stored in a flexible pouch, comprising a housing, suspension means in said housing for receiving the pouch and holding the pouch such that major surface areas of the pouch are accessible, heat transfer means oriented to address the major surface of the pouch including a heat transfer fluid such that upon contact with said fluid the product within the pouch approaches the temperature of the fluid, and means for circulating the product in the pouch to minimize thermal gradients within the pouch during heat transfer.

Viewed from a second vantage point, it is an object of the present invention to provide a device for transferring heat between an article at one temperature and a fluid maintained at another temperature which includes a membrane interposed between the fluid and the article, the membrane isolating the fluid from the article such that the fluid contact with the article is indirect and temperature change passes through the membrane, and means for pulsing the fluid is provided oriented to impinge the article through the membrane, whereby the fluid pulsing means induces thermal circulation into the article for better heat transfer.

Viewed from a third vantage point, it is an object of the present invention to provide a device for rapidly thawing frozen transfusion material such as blood or plasma to a liquid state for immediate use in an operation as needed which comprises a reservoir adapted to receive thawing fluid therewithin and isolated from the transfusion material by a membrane, the membrane interposed between the transfusion material and the reservoir to preclude contact with the fluid, and pulsing means to deliver the thawing fluid against the transfusion material by pulsing passing through the membrane, the pulsing means and the thawing fluid collectively defining a massaging means against the transfusion material to promulgate rapid thawing of the transfusion material by circulating thawed fractions of the transfusion material about frozen parts for better heat transfer.

Viewed from a fourth vantage point, it is an object of the present invention to provide a method for rapidly thawing transfusion fluid from a frozen state to a transfusion temperature, the steps including pulsing thermal fluid against a pouch containing the frozen transfusion fluid to raise the temperature of the transfusion fluid and circulate the transfusion fluid within the pouch as it thaws and initially maintaining the thermal fluid at a temperature greater than the temperature of the frozen transfusion fluid but less than or equal to the transfusion temperature.

These and other objects will be made manifest when considering the following detailed specification when taken in conjunction with the appended drawing figures.

DESCRIPTION OF PREFERRED EMBODIMENTS

Figure 1:
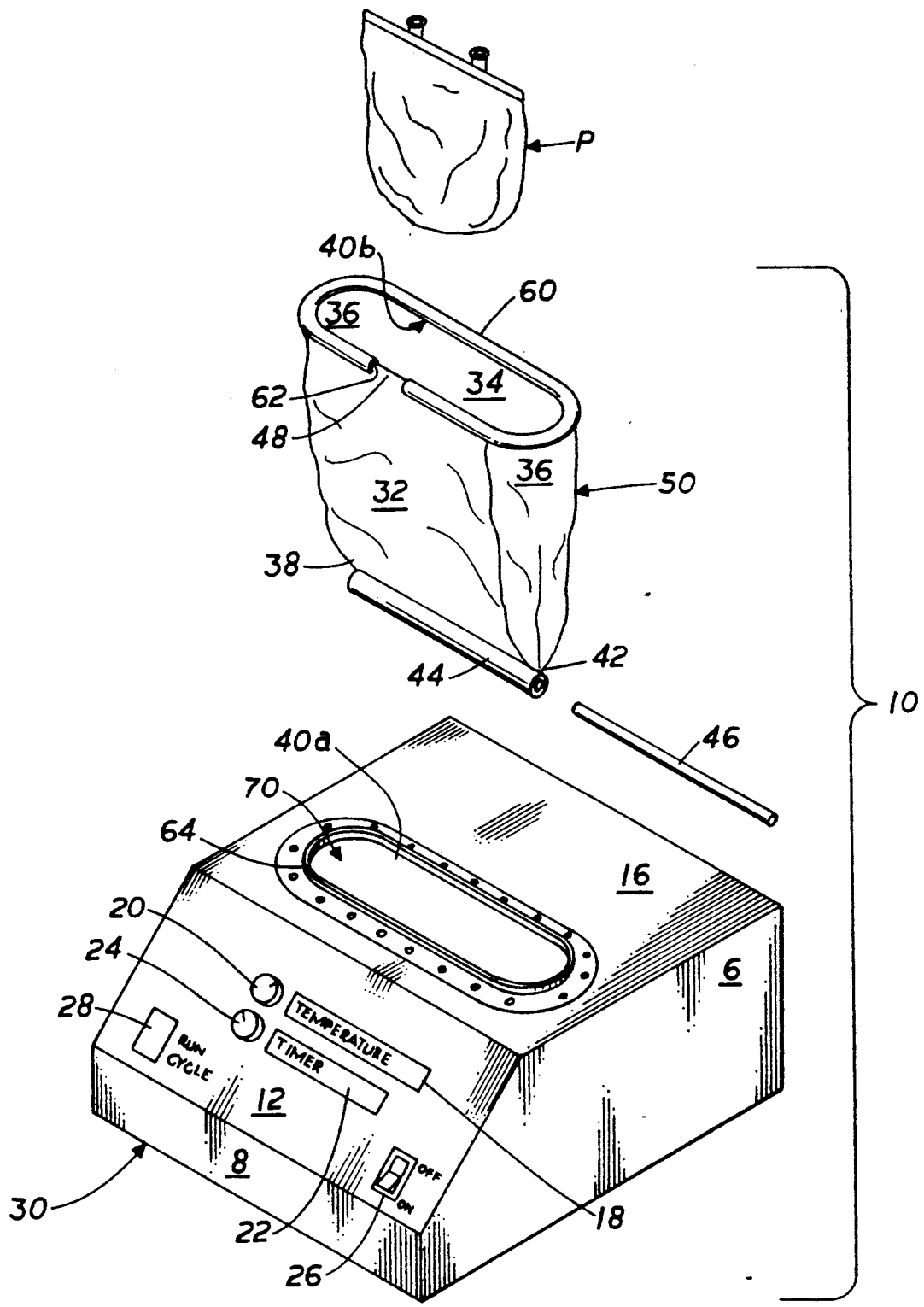
FIG. 1 is a perspective view, showing exploded parts of the apparatus according to the present invention.

Referring to the drawings now, wherein like reference numerals refer to like parts throughout the various drawing figures, reference numeral 10 is directed to the device for thawing frozen transfusion material according to the present invention.

In essence, the device 10 is formed from a housing 30 having a control panel 12 on one exposed surface thereof and an opening 40a on a top wall 16 and within which a flexible membrane 50 is provided. The membrane 50 occludes an interior 70 of the housing 30 from an exterior. The membrane 50 is removably inserted to depend within the interior 70 so that a pouch P can be removably inserted into the membrane 50 and therefore into interior 70. The pouch P is then exposed to heat exchange fluid F and fluid pulsation through the membrane 50.

Figure 2:
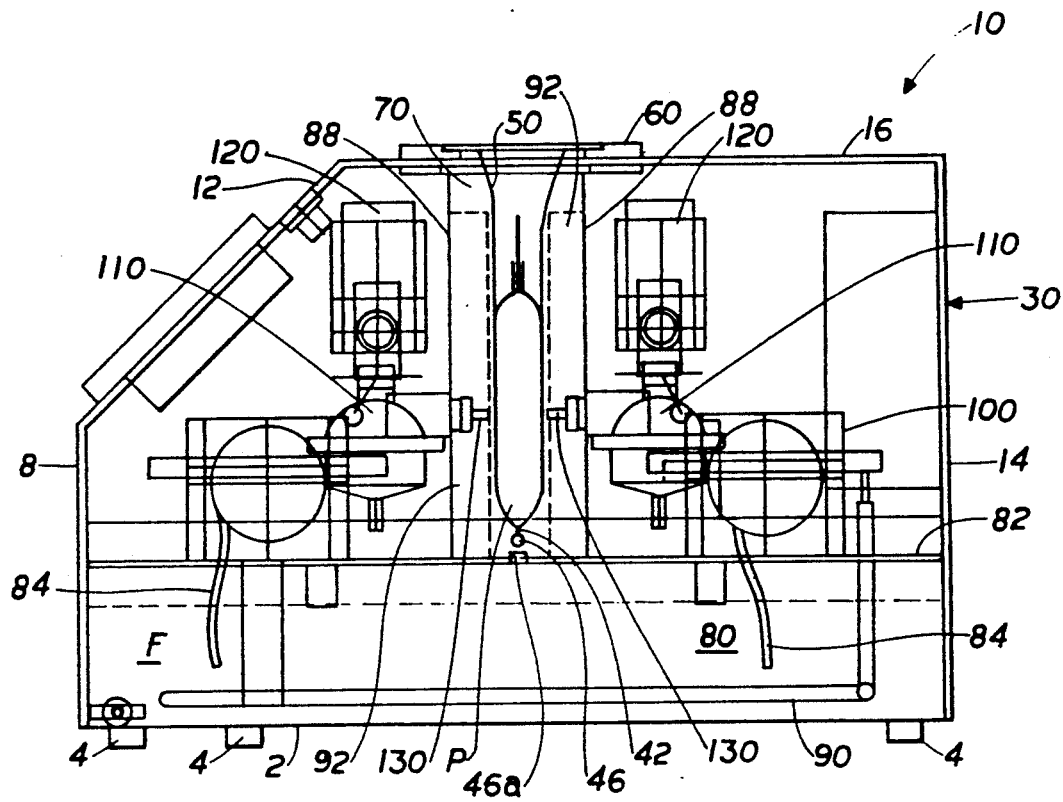
FIG. 2 is transverse longitudinal sectional view of the apparatus according to the present invention showing a loading or removing cycle.
Figure 3:
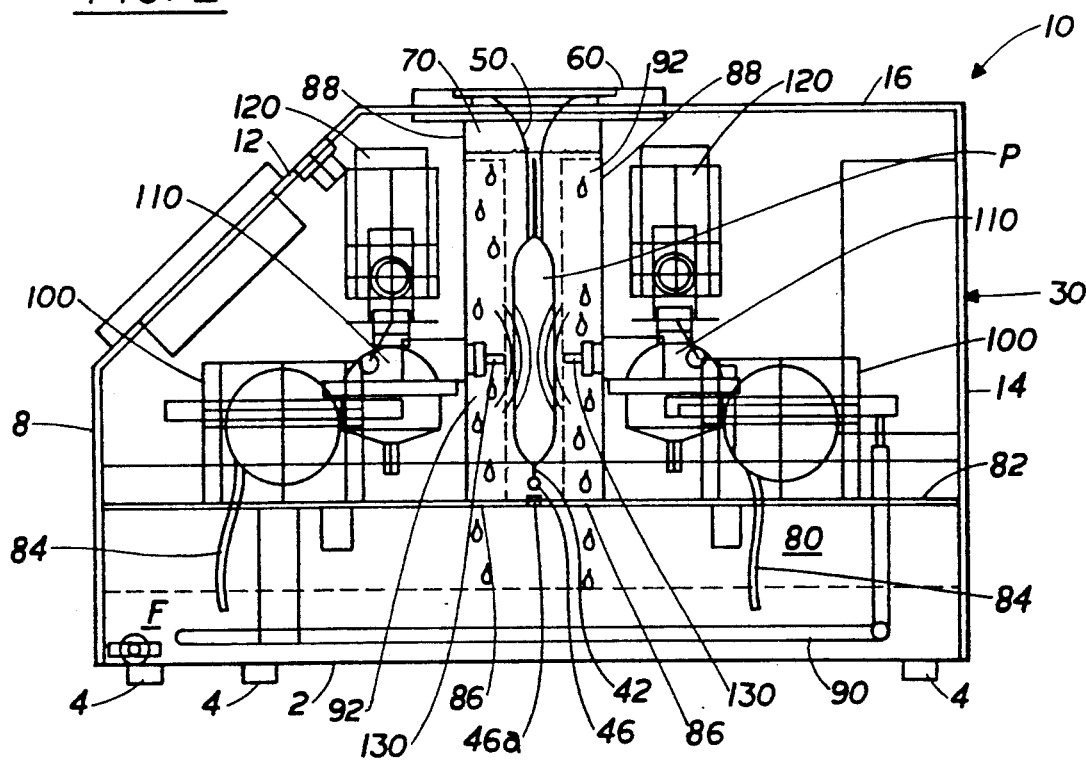
FIG. 3 is a view similar to FIG. 2 schematically showing the device in operation.
Figure 4:
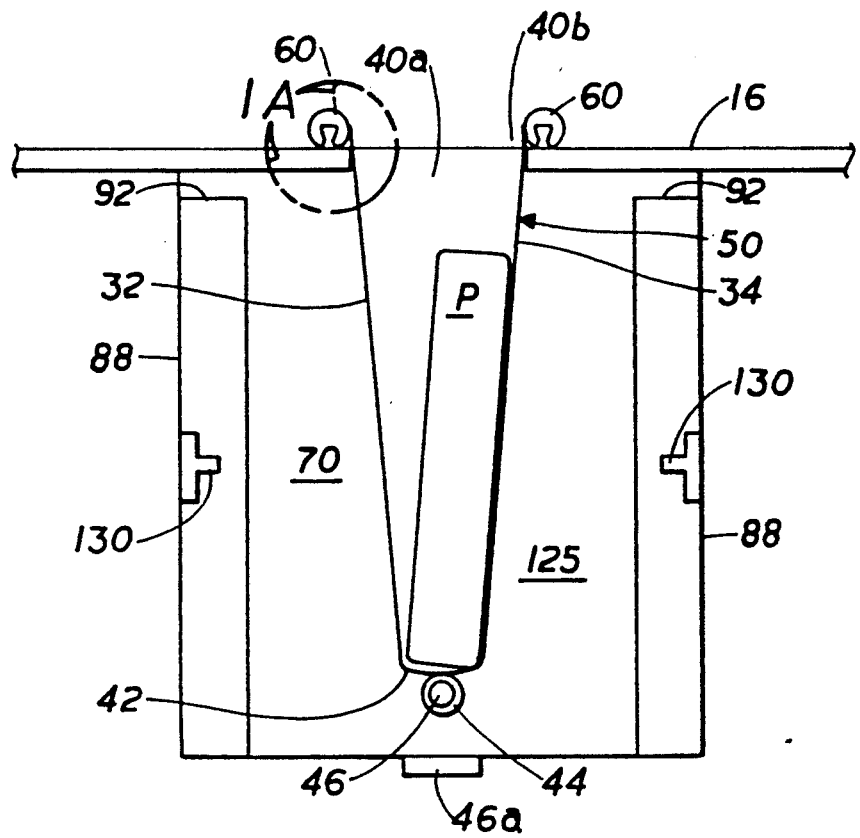
FIG. 4 is a detail of a portion of the FIG. 2 structure.
Figure 5:
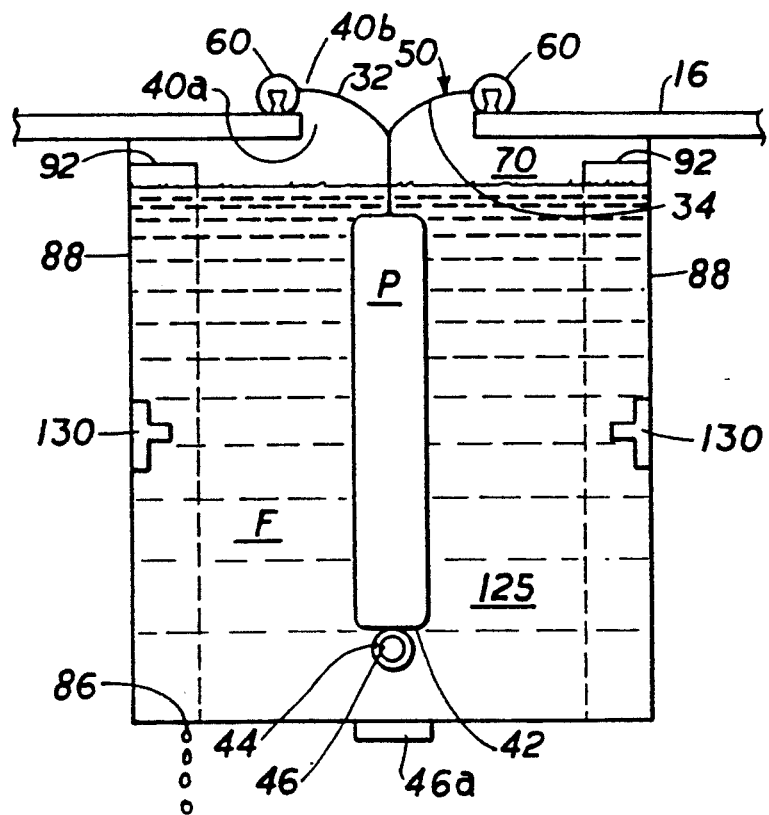
FIG. 5 is a detail of a portion of the FIG. 3 structure.

More specifically, the housing 30 from a side view is a substantially rectangular construct having one corner of the rectangular construct truncated or mitered providing an inclined surface upon which a control panel 12 is provided. With reference to FIGS. 1 through 3, the housing 30 includes a bottom wall 2 supported on a surface by means of feet 4 disposed on a bottom surface of wall 2. The bottom wall 2 is preferably substantially rectangular in configuration and planar and has two parallel side edges from which extend two vertical side walls 6 one each on opposed side edge extremities. In addition, a front wall 8 extends up from a front edge of the bottom wall 2. A rear wall 14 extends up from a rear edge of the bottom wall 2 which is parallel to the front wall edge. A top wall 16 is provided which joins the side walls 6 and rear wall 14. Had the front wall 8 been similarly joined with the top wall 16, a orthorhombic construct would have been provided. Instead, an inclined control panel wall 12 extends from a top edge of the front wall 8 to a forward edge of the top wall 16. Thus, to accommodate the control panel 12, the side walls 6 are truncated at corners adjacent the control panel 12 to complete the housing 30.

The control panel 12 supports a temperature indicator 18 used to indicate the temperature of the working, thawing fluid F in a manner to be described. In addition, a temperature control 20 allows alteration of the temperature of the working fluid F as reflected by the temperature indicator 18. The control panel 12 also supports a timer 22 indicating the amount of time that the working fluid F will circulate (in a manner to be described) and a timer control 24 is provided on the panel 12 to alter the amount of time that will define one cycle for the thawing process. If desired, a commercially available digital touch pad could be used for not only the timer and its control but also for the temperature and its control. An on/off switch 26 is operatively coupled to provide power to the device 10 and is also supported on the control panel 12. An indicator 28 is also provided on the control panel 12 and indicated whether or not the device 10 is in the midst of a cycle for thawing frozen material. The indicator 28 may be in the form of a pilot light and/or may include an audible alarm.

As mentioned briefly, the housing 30 includes an opening 40a through which a membrane 50 is provided which occludes the interior 70 defined by the housing walls 2, 8, 12, 14, 16 discussed hereinabove. In essence, the membrane 50 is sufficiently flexible to receive a thermolabile product such as a pouch P of blood, plasma, platelets, pharmaceutical materials or tissue therewithin so that it can be thawed expeditiously. The membrane 50 is formed from a front panel 32, a rear panel 34, two side panels 36 and a bottom panel 38. The two side panels 36 and bottom panel 38 connect the front and rear panels 32, 34 together respectively at side and bottom edges of the front and rear panel 32,34 so that an enclosure is provided having an upper opening 40b which is substantially complemental to the opening 40a of the housing 30.

In addition, the membrane 50 preferably includes a skirt 42 of material depending from the bottom panel 38. The skirt 42 has a sleeve 44 at a lowermost extremity of substantially cylindrical configuration and substantially coextensive with the width of both the front and rear panels 32, 34. A hold-down rod 46 is inserted within the sleeve 44 and is used as an anchor to offset the effects of buoyancy associated with the thawing fluid F to be described hereinafter. The hold down rod 46 may have a magnetic component which cooperates with another magnet 46a, located on a top surface of a shelf 82 to offset buoyancy. Another version may embody the rod 46 as substantially U-shaped with legs extending upwardly, parallel to the side panels 36.

Figure 1A:
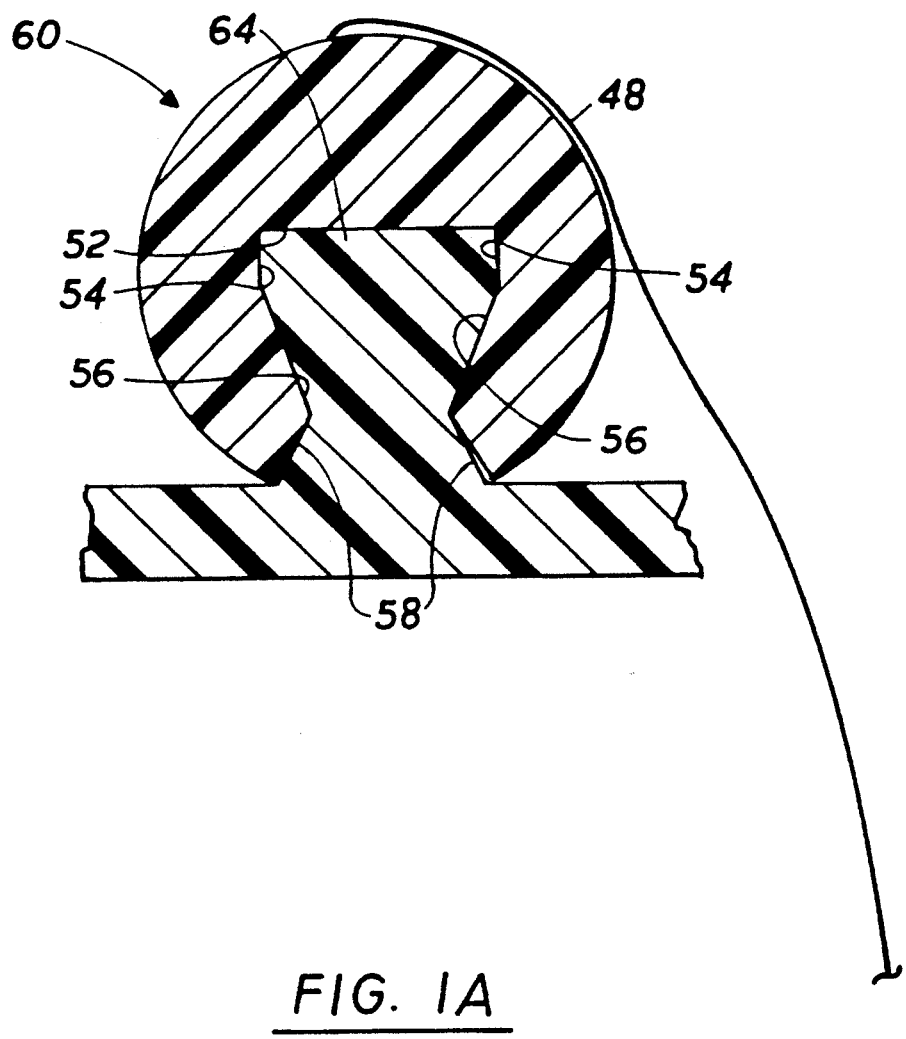
FIG. 1A is directed to a detail of FIG. 4 along lines 1A—1A in section.

The topmost portion of the membrane 50 adjacent the opening 40b includes a peripheral flange 48 defining a turnout of the membrane 50. This flange 48 supports a snap-on coupling 60 having an oval configuration which is somewhat complemental to the opening 40b of the flexible membrane 50. The coupling 60 also circumscribes the opening 40a on the housing 30. Coupling 60 can suspend beneath flange 48 or be integrally formed therewith or be bonded thereto. The snap-on coupling 60 has an outer profile of substantially circular configuration, shown best in FIG. 1A, with an opening 62 to define an interior therewithin defining a retention mechanism which adheres to a ridge 64 on the top wall 16 of housing 30.

More specifically, the interior of the coupling 60 is formed from a pair of spaced guide channels 58 which diverge outwardly and which lead to retention channels 56 which diverge inwardly. Two parallel, facing support channels 54 communicate with the retention channels 56 and terminate in an abutment channel 52 which rests on a top surface of ridge 64 that circumscribes the outer periphery of the housing opening 40a. Thus, whereas the coupling 60 defines a recess, the ridge 64 defines a projection with a contour complemental to the snap-on channel 60 for frictional retention therebetween. The construction thus far enumerated with respect to the snap-on channel 60 and ridge 64 lend themselves to the expeditious removal of the flexible membrane 50 should it become contaminated when a pouch of thermolabile fluid (such as blood) had fractured and is revealed during the thawing process because it contaminates the interior of the flexible membrane 50. Thus, the ridge 64 defines a male projection complemental to the recess integrally formed on the snap-on coupling 60 and allows rapid replacement.

Attention is now directed to FIGS. 2 and 3 with respect to the operation mechanism by which a pouch P of frozen material can be inserted into the membrane 50 located within the interior 70 of the device 10 and rapidly thawed to an optimal temperature for transfusion or other purposes. It is to be noted that the membrane 50 is characterized as one which is extremely flexible and yields to hydrostatic pressure induced by the presence of the thawing fluid F on an outside surface thereof so that the pouch P (when placed within the interior of the membrane 50) will have the membrane 50 collapse around the pouch P and conform to the configuration of the pouch P with no air gaps for optimal heat transfer. One suitable material for this membrane 50 is polyetherurethane, although other thin hydrostatically flexible material such as Teflon ® would be serviceable.

Comparison between FIGS. 2 and 3 shows the membrane 50 collapsing around the pouch P and conforming to the pouch P in the presence of hydrostatic pressure. More specifically, a sump 80 is provided at a lowermost portion of the device 10 and collects the thawing fluid F therewithin. Typically, a silicone heat transfer fluid F would be adequate to operate within the contemplated temperature range of typically −30° C. to +37° C. The sump 80 holds the fluid F therewithin. An immersion heater 90 maintains the thawing fluid F at a substantially constant temperature, typically the target temperature of the pouch P when it is to be subsequently used for example by transfusion. As mentioned earlier, the temperature of the fluid F can be controlled on the control panel 12 by an appropriate mechanism.

A pump 100 is placed above the sump 80 and supported on an intermediate platform 82 supported in the housing 30. The pump 100 includes an inlet 84 which extends into the fluid F contained in the sump 80. The inlet 84 delivers the thawing fluid F to the pump 100 so that it can be administered on an exterior surface of the membrane 50 (i.e. on a surface of the membrane 50 opposite from that surface of the membrane 50 contacting the pouch P) following the preferred manner. The pump 100 administers thawing fluid F to a geometrical center of the pouch P ("through" the membrane 50) by means of a nozzle jet 130. By geometrical center it is meant the surfaces of the pouch P remote from side edges thereof which define a periphery. By the jet 130 impinging on the pouch P along major surfaces thereof and preferably at the geometrical center of the pouch P, the core of the thermolabile fluid contained within the pouch P will be rapidly thawed and circulated in the following manner.

It is preferred that the nozzle jet 130 pulse thawing fluid F at the geometrical center of the membrane 50 and pouch P. In order to achieve same, the nozzle 130 has interposed between its outlet and the pump 100 a solenoid valve 120 and a surge chamber 110. The surge chamber 110 is closer to the pump 100 than the solenoid valve 120. In use and operation, as the pump 100 provides continuous fluidic pressure by delivering thawing fluid F from the sump 80 through the pump 100 and to a surge chamber 110. Cyclic opening and closing of the solenoid valve 120 provides pulses from the nozzle jet 130 hitting the geometrical center of the pouch P.

The surge chamber 110 is configured in such a manner that increasing fluidic pressure exerted by the pump 100 will be stored as a potential energy in the surge chamber 110 whereupon, by opening of the solenoid valve 120, the potential energy within the surge chamber 110 converts immediately to kinetic energy and vents outwardly through the nozzle jet 130. The nozzle jet 130 may have appropriate nozzle geometry such as converging, diverging throat areas to achieve acceleration at its outlet and an appropriate "needle" or "spray" pattern.

Figure 7:
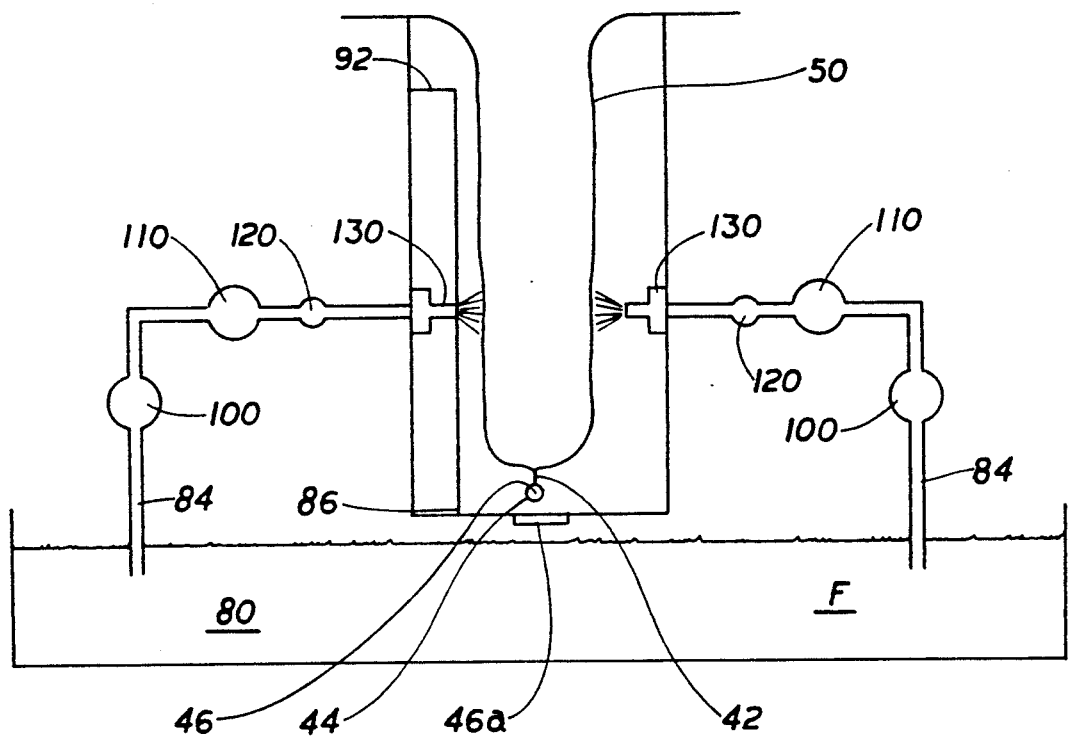
FIG. 7 shows a fluid flow schematic.

In a preferred form of the invention, a pair of nozzles 130, one each disposed on opposite major surfaces of the membrane 50 and therefore the pouch P are provided. One way to achieve two nozzles 130 operating in concert would be to have a solitary pump 100 delivering thawing fluid F to both of the nozzles 130 with a manifold delivering to the nozzle jets 130 simultaneously. It is preferred that each nozzle 130 administer a pulse of thawing fluid F to the geometrical center of the membrane 50 at the same time, to preclude oscillation or rocking of the membrane 50 back and forth. However, a branch manifold such as just described may provide an unwanted reduction in pressure of the nozzle 130 output. In such an event, a pair of pumps 100 (shown in the drawing FIGS. 2, 3 and 7) along with a pair of surge chambers 110 and solenoid valves 120 are provided, with the firing of the solenoid valves 120 synchronized with electrical means (not shown) to achieve simultaneous firing of the nozzles 130.

FIG. 3 reflects another preferred scenario for the most expeditious thawing of the contents within the pouch P. It is contemplated that the rate at which the fluid F contacts the membrane 50 and pouch P is greater than the ability of the thawing fluid F to be drained from a weep hole 86 placed through the platform 82 and thence to the sump 80. The distribution of the thawing fluid F by means of the nozzles 130 will thus cause accumulation of the fluid F within a chamber 125 circumscribing the membrane 50 and defined by partitions 88 (located forward and rearward of the membrane 50) and the side walls 6. Partitions 88 allow the liquid level of thawing fluid F to rise to ensconce the membrane 50 and cause the membrane 50 to collapse upon the pouch P by hydrostatic pressure. Even with the presence of thawing fluid F within this chamber 125, the nozzle jets 130 are configured to still provide pulsing shocks through the fluid F and to the membrane 50 and therefore the pouch P. At least one spillway 92 encourages the fluid F, once it has risen to the level of the spillway 92, to re-enter the sump 80 to maintain the temperature of the thawing fluid F substantially constant at a target temperature. Note that the weep hole 86 is preferred to communicate with the spillway 92. This beneficially controls the rate at which fluid F seeps from the chamber 125.

Figure 6D:
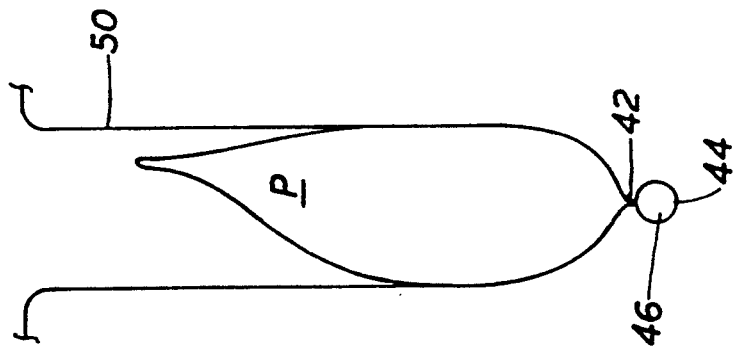
FIGS. 6A, 6B, 6C and 6D explain the phenomena of the pulsation and internal circulation according the the instant invention.
Figure 6C:
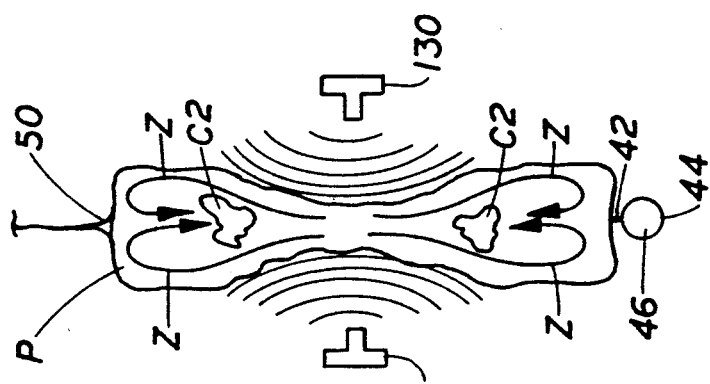
Figure 6B:
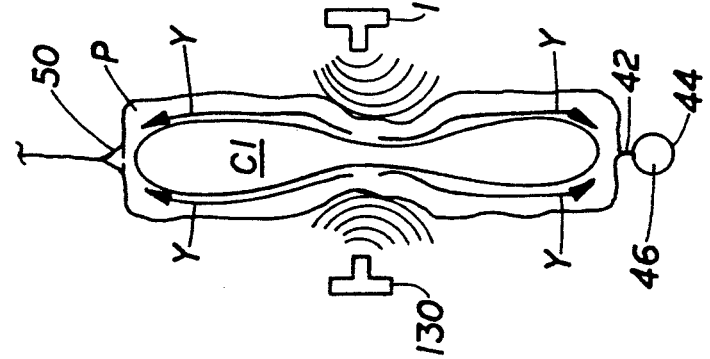
Figure 6A:
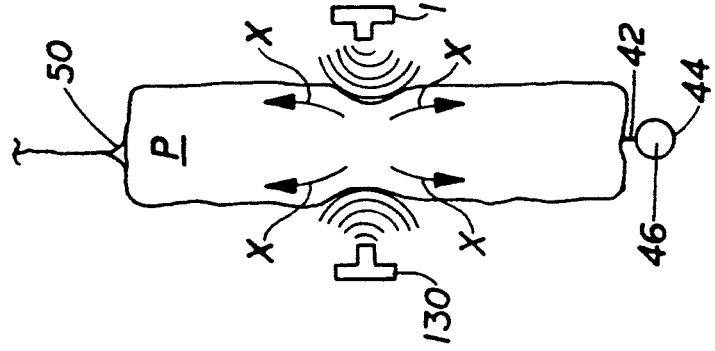

FIGS. 6A through 6D reflect the various stages in the thaw cycle for a pouch P of thermolabile material. FIG. 6A reflects the scenario when the membrane 50 has already been ensconced in thermal fluid F and has constricted around the pouch P and the nozzle jets 130 are continuing to work on the pouch P through the membrane 50. As shown therefore, in FIG. 6A, the pouch P and the membrane 50 have a somewhat rectangular configuration or the exact configuration of the frozen pouch P. The initial thermal pulsing causes a minor indentation at the area of impingement with the nozzle jets 130 and liquid thawed from the pouch P is starting to circulate, as shown by arrows X, between the skin of the pouch P and the frozen transfusible fluid. In FIG. 6B there has been sufficient melting at the core of the pouch P to encourage greater fluid circulation of the thermolabile fluid such as shown by the arrows Y and when contrasted with the arrows X of FIG. 6A. There is still, however, a core of material $C_1$ which is substantially shaped like a FIG. "8" in cross-section and the outer fluid is thicker, working and diminishing the size of the frozen core $C_1$. FIG. 6C shows the scenario where only a minor frozen core $C_2$ exists and the fluid migration forces Z are pushing the frozen core $C_2$ closer to the pulsating center. Finally, FIG. 6D shows the pouch P when it is completely thawed and in a flaccid state.

Moreover, having thus described the invention, it should be apparent that numerous structural modifications and adaptations may be resorted to without departing from the scope and fair meaning of the instant invention as set forth hereinabove and as described hereinbelow by the claims.

I claim:

1. A device for transferring heat between an article at one temperature and a fluid maintained at another temperature, comprising, in combination:

a membrane interposed between said fluid and the article, said membrane isolating said fluid from the article such that fluid contact with the article is indirect and temperature change passes through the membrane, and means for pulsing said fluid oriented to impinge the article through the membrane, said fluid pulsing means inducing thermal circulation into the article for better heat transfer.

2. The device of claim 1 wherein said membrane includes means for rapid replacement of said membrane within said device should the article placed within said membrane for heat transfer be fractured and expose its contents to said membrane.

3. The device of claim 2 wherein said pulsing means includes a plurality of nozzles oriented to impinge directly on said membrane and therefore indirectly on the article such that kinetic energy of said fluid is dissipated by contact against the membrane directly and indirectly on the article.

4. The device of claim 3 wherein two said pulsing nozzles are provided on diametrically opposed sides of said membrane and the article.

5. The device of claim 4 wherein said two nozzles include means to synchronize and operate in concert such that each said nozzle emits a quantum of fluid at the same instant, and said nozzles are equally distant from said membrane for simultaneous contact on said membrane.

6. The device of claim 5 wherein said membrane is oriented within a compartment which allows fluid build-up against said membrane and said compartment includes a spillway oriented above the pouch which facilitates recirculation of the fluid from the compartment to an underlying sump.

7. The device of claim 6 wherein said compartment includes a weep hole drain means to return the fluid back to said sump in addition to said spillway.

8. A device to rapidly thaw frozen transfusion material such as blood, platelets or plasma or tissue or pharmaceutical products such as antibiotics or other thermolabile product to a liquid state for immediate use as in an operation and as needed comprising, in combination:

a reservoir adapted to receive thawing fluid therein and isolated from the transfusion material by a membrane means, said membrane means interposed between the transfusion material and said reservoir to preclude contact with said thawing fluid, and pulsing means to deliver said thawing fluid against the transfusion material and through said membrane, said pulsing means and said thawing fluid collectively defining a massaging means against the transfusion material to promulgate rapid thawing of the transfusion material by circulating thawed fractions of the transfusion material about still frozen parts of the transfusion material for better heat transfer.

9. The device of claim 8 wherein said pulsing means delivers said thawing fluid at a rate which allows fluid build-up against membrane, thereby providing hydrostatic pressure which causes said membrane to collapse against the transfusion material, and said reservoir includes drainage means for removing the accumulating said fluid.

10. The device of claim 9 including means to maintain constant a target temperature for said transfusion material including heating means for said thawing fluid set at a temperature coincident with said target temperature for said transfusion material.

11. The device of claim 10 including a sump in said reservoir to receive said thawing fluid during the course of its circulation against said membrane, said sump communicating with a sump pump for circulating said thawing fluid to said pulsing means, and energy storage means interposed between said pump and a fluid outlet of said pulsing means.

12. The device of claim 11 wherein said energy storage means includes a surge chamber disposed adjacent said pump, downstream therefrom with respect to said sump and a solenoid value interposed between said sump and said fluid outlet whereby timely opening of said solenoid valve discharges pressure built-up within said surge chamber and induced by said pump to provide added velocity to said thawing fluid as it impinges upon said membrane.

13. The device of claim 12 wherein said pulsing means includes means for synchronizing a plurality of said pulsing means for simultaneous impingement against said membrane.

14. A method for rapidly thawing transfusion fluid from a frozen state to a transfusion temperature, the steps including:

pulsing thermal fluid against a pouch containing the frozen transfusion fluid to raise the temperature of the transfusion fluid and circulate within the pouch the transfusion fluid as it thaws, and initially maintaining the thermal fluid at a temperature greater than the temperature of the frozen transfusion fluid but less than or equal to the transfusion temperature.

15. The method of claim 14 including immersing the pouch within the thermal fluid.

16. The method of claim 15 including circulating the thermal fluid from its intimate contact with the pouch to a source of heat, and reheating the thermal fluid and recirculating the thermal fluid.

17. The method of claim 16 including pulsing thermal fluid against the pouch in synchronicity with another pulsation means to provide synchronous pulsing.

18. The method of claim 17 including isolating the pouch from the thermal fluid by interposing a flexible membrane therebetween and deforming the membrane against the pouch in the presence of the thermal fluid.

19. The method of claim 18 including orienting the membrane such that it can be rapidly redeployed and removing the membrane upon contamination of the membrane by a defective pouch and reinstalling another membrane in its place.

* * * * *